(12) United States Patent
McFarlane

(10) Patent No.: US 6,908,454 B2
(45) Date of Patent: Jun. 21, 2005

(54) ANCHORING ASSEMBLY FOR A MEDICAL INSTRUMENT

(75) Inventor: Richard H. McFarlane, Singer Island, FL (US)

(73) Assignee: Taut, Inc., Geneva, IL (US)

( * ) Notice: Subject to any disclaimer, the term of this patent is extended or adjusted under 35 U.S.C. 154(b) by 0 days.

(21) Appl. No.: 10/366,679

(22) Filed: Feb. 13, 2003

(65) Prior Publication Data

US 2003/0158572 A1 Aug. 21, 2003

Related U.S. Application Data

(60) Provisional application No. 60/357,277, filed on Feb. 15, 2002.

(51) Int. Cl.$^7$ .......................... A61M 5/32; A61M 29/00
(52) U.S. Cl. ..................... 604/178; 604/96.01; 604/104
(58) Field of Search .............................. 604/96.01, 104, 604/105, 106, 107, 108, 164.01, 164.03, 164.04, 164.09, 164.1, 164.11, 174, 178, 264, 272; 606/108, 167, 168, 169, 170, 171, 191, 192, 198

(56) References Cited

U.S. PATENT DOCUMENTS

| | | |
|---|---|---|
| 2,912,981 A | 11/1959 | Keough |
| 3,039,468 A | 6/1962 | Price |
| 3,253,594 A | 5/1966 | Matthews et al. |
| 3,528,869 A | 9/1970 | Dereniuk |
| 3,640,281 A | 2/1972 | Robertson |
| 3,656,486 A | 4/1972 | Robertson |
| 3,896,816 A | 7/1975 | Mattler |
| 3,952,742 A | 4/1976 | Taylor |
| 3,961,632 A | 6/1976 | Moossun |
| 4,003,382 A | 1/1977 | Dyke |
| 4,077,412 A | 3/1978 | Moossun |
| 4,083,369 A | 4/1978 | Sinnreich |
| 4,393,873 A | 7/1983 | Nawash et al. |
| 4,861,334 A | 8/1989 | Nawaz |
| 5,002,557 A | 3/1991 | Hasson |
| 5,122,122 A | 6/1992 | Allgood |
| 5,147,316 A * | 9/1992 | Castillenti ............... 604/164.04 |
| 5,176,697 A | 1/1993 | Hasson et al. |
| 5,300,036 A | 4/1994 | Mueller et al. |
| 5,397,335 A | 3/1995 | Gresl et al. |
| 5,402,772 A | 4/1995 | Moll et al. |
| 5,409,896 A | 4/1995 | Ammann et al. |
| 5,429,598 A | 7/1995 | Waxman et al. |
| 5,697,946 A | 12/1997 | Hopper et al. |
| 5,700,243 A * | 12/1997 | Narciso, Jr. ............. 604/102.01 |
| 5,868,708 A | 2/1999 | Hart et al. |
| 5,957,888 A * | 9/1999 | Hinchliffe .................... 604/117 |
| 5,980,493 A | 11/1999 | Smith et al. |
| 6,019,746 A | 2/2000 | Picha et al. |
| RE36,702 E | 5/2000 | Green et al. |
| 6,375,637 B1 * | 4/2002 | Campbell et al. ........... 604/103 |

* cited by examiner

*Primary Examiner*—Nicholas Lucchesi
*Assistant Examiner*—Mark K. Han
(74) *Attorney, Agent, or Firm*—Malloy & Malloy, P.A.

(57) ABSTRACT

An anchor assembly for retaining a cannula or other medical instrument within a body cavity and including an inflatable member selectively disposed between an expanded position and a collapsed position. A mounting assembly is cooperatively disposed and structured with a base, underlying the inflatable member, so as to mechanically attach the inflatable member to an exterior of the cannula. The mechanical attachment is accomplished by one or more retaining segments on the inflatable member being disposed in a compressed or sandwiched orientation between the base and the mounting assembly.

24 Claims, 3 Drawing Sheets

ANCHORING ASSEMBLY FOR A MEDICAL INSTRUMENT

CLAIM OF PRIORITY

The present application is based on and a claim to priority is made under 35 U.S.C. Section 119(e) to a provisional patent application currently pending in the U.S. Patent and Trademark Office and having Ser. No. 60/357,277 and a filing date of Feb. 15, 2002.

BACKGROUND OF THE INVENTION

1. Field of the Invention

The present invention is directed to an anchor assembly for retaining a medical instrument within an anatomical cavity, wherein the anchor assembly comprises a mechanical attachment of an inflatable member to the exterior of the medical instrument. The mechanical attachment eliminates or at least minimizes the reliance on adhesive and other conventional types of connections, thereby greatly reducing the assembling and manufacturing costs, while eliminating or significantly reducing the failure or inadvertent detachment of the inflatable member from its operative position on the instrument.

2. Description of the Related Art

The use of various types of anchoring devices on medical instruments, in order to maintain the instrument on the interior of a body cavity or in a predetermined location relative to other organs of the body, is well known. One prevalent category of anchoring devices includes the use of an inflatable "balloon" or like member formed of an expandable material and secured to an exterior portion of the instrument with which it is associated. Examples of medical instruments incorporating such inflatable anchoring devices include trocars, which are used in laparoscopic or endoscopic surgery, and in particular, the cannula portion of the trocar, as well as retention catheters.

In this latter category, i.e., retention type catheters, a flexible or resilient body portion has an elongated inflating lumen which directs fluid (e.g., gas) under pressure into an interior the inflatable balloon or like structure. Upon inflation, the balloon will extend radially outward so as to effectively retain the catheter in the intended position. Similarly, trocar structures are used in minimally invasive surgical procedures. In use, a cannula portion of the trocar enters a body cavity and is effectively retained or "anchored" into an intended position by subjecting the interior of the anchoring balloon to pressurized fluid.

Previously, the elastic material from which the inflatable balloons or like members were formed was a rubber or latex material. As such, the degree of pressurization of the inflating fluid was maintained within certain acceptable limits. However, more recently the inflatable balloons or like structures have been formed of a plastic material including, but not limited to, polyurethane, polyvinyl chloride and various copolymers thereof. It was soon discovered that balloons formed from the aforementioned types of plastic materials require higher inflation pressures than conventional latex balloons. While the inflating fluid could easily be supplied to the interior of the balloon or other inflatable retention device at an increased pressure, other disadvantages or problems associated therewith developed.

More specifically, the structural features associated with the attachment or securement of the inflatable anchors to the exterior of the medical instrument are recognized as being problematic. The aforementioned disadvantages are primarily associated with failure or malfunctioning of the inflatable member by virtue of them becoming detached when expanded or inflated, not unlike the "blow-out" of a tire. As a result, a variety of different techniques, wrapping or winding structures, etc. were developed in an attempt to provide a reliable means of attaching an inflatable member to the cannula portion of a trocar, while not overly complicating the manufacturing process for such anchoring devices.

Known structures associated with the attachment of inflation anchors or like expandable structures typically include the use of adhesives, molding and/or heat sealing techniques, which may used independently or in combination with one another. In addition, an inflatable anchoring structure associated with known, commercially available trocar assemblies utilizes an adhesive securement in combination with a wrapping or binding of wound suturing material. The suturing material is applied to opposite ends or other appropriate portions of the inflatable retention device in order to maintain its secured engagement on the exterior of the cannula portion of the trocar or other type of instrument.

Despite the extensive time and effort dedicated to the effective attachment or mounting of an inflatable, balloon type retention member on medical instruments, the above set forth problems and disadvantages associated with the costs of assembly and manufacture as well as the rate of failure of such anchoring devices still exists. More specifically, detachment problems associated with inflatable anchors as used on a variety of known and commercially available trocar assemblies, retention catheters, etc., is all too common. Therefore, there is a significant and long recognized need for an anchoring assembly capable of being used on a trocar or other medical instrument which is safe, reliable and which is not unduly expensive or complicated to manufacture and produce. If any such improved anchoring assembly were developed, it should be capable of stabilized and reliable attachment to an exterior or other appropriate portion of an associated medical instrument in a manner which overcomes the problems associated with conventional or known inflatable retention devices. In addition, any such improved anchor assembly would ideally include the attachment of an inflatable member to an instrument in a manner capable of consistently withstanding inflating gases supplied at commonly used or increased pressures.

SUMMARY OF THE INVENTION

The present invention is intended to address these and other needs which remain in the art and is directed to an anchoring assembly of the type typically utilized to maintain the cannula portion of trocars, retention catheters and/or other medical instruments in a preferred or intended location on the interior of a body cavity or in retaining engagement with one or more organs within the body cavity. The anchoring assembly of the present invention is of the inflatable type typically comprising an inflatable "balloon", bag or like member, capable of being selectively disposed between an outwardly extending, expanded position and a collapsed position. The medical instrument associated with the anchor assembly of the present invention may, therefore, be maintained in an intended position within a body cavity by selectively orienting an inflatable member into the expanded or inflated position. Moreover, the anchor assembly of the present invention is structured to overcome many of the disadvantages and problems associated with the failure of known or conventional inflatable anchoring or retaining devices by mechanically securing the inflatable member to an exterior of the instrument with which it is associated.

More specifically, the anchoring assembly of the present invention comprises a mounting assembly secured to an exterior portion of the cannula or other instrument. In at least one preferred embodiment, the mounting assembly includes a first mounting member and a second mounting member both disposed in overlying, at least partially surrounding relation to exterior surface portions of the cannula or instrument. In addition, a base is also secured in overlying relation to an exterior surface the instrument on which the anchoring assembly is mounted. The base is disposed in adjacent but spaced relation to the mounting assembly including each of the first and second mounting members.

Moreover, the base is disposed in underlying relation to the inflatable member and is positioned and structured to substantially confront interior surface portions of the inflatable member, such as when the inflatable member is in the aforementioned collapsed position. The base and the inflatable member may be considered to have a generally similar or corresponding overall configuration at least to the extent of being annularly formed so as to extend in surrounding, overlying relation to an exterior portion of the associated instrument. Such an annular configuration of at least the inflatable member facilitates the outward, radially oriented disposition of the inflatable member when in its expanded position. Also, the base may comprise a bushing or like structure having a closed, continuous configuration and is cooperatively disposed and structured to facilitate the mechanical attachment of the inflatable member in its intended operative position.

As set forth, above at least one preferred embodiment of the anchor assembly comprises a first mounting member and a second mounting member. The base is positioned adjacent and in spaced relation to each of the first and second mounting members by virtue of its disposition there between. As a result, a predetermined spacing exists between the base and the mounting assembly. This predetermined spacing is preferably defined by two retaining spaces, each disposed or formed between different ones of the first and second mounting members and a corresponding portion of the base.

In order to accomplish the primarily mechanical securement or connection of the inflatable member in its intended, operative position, the inflatable member includes a retaining portion formed thereon or connected thereto. The retaining portion preferably includes at least two retaining segments which may be disposed or defined by peripheral segments of opposite ends of the inflatable member. Each of the retaining segments are correspondingly disposed and configured to be received within different ones of the aforementioned retaining spaces defined between the base and each of the first and second mounting members.

The cooperative structuring of the first and second mounting members and the base, as well as their disposition relative to one another, facilitates the secured retention of the retaining segments by the mechanical locking and sealing thereof in a sandwiched or at least partially compressed orientation within corresponding ones of the retaining spaces. As a result, a reliable securement of the inflatable member to the exterior of the trocar cannula or other medical instrument is accomplished using primarily, if not exclusively, a mechanical attachment as versus the use of adhesive, heat sealing techniques or exterior binding with wound suture, thread, cord, or like material.

The objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying Figures, the present invention is directed to an anchor assembly, generally indicated as 10, structured to be secured to a trocar assembly, generally indicated as 12, or to another type of medical instrument. As will be more fully explained herein, the instruments 12 are of the type intended to be maintained in a predetermined position or orientation within a body cavity. Therefore, while the anchor assembly 10 is described herein as being mounted about the exterior of a cannula portion 14 of the trocar assembly 12, the anchor assembly 10 of the present invention could be utilized with a variety of medical instruments including, but not limited to a retention catheter or like device.

Figure 1:
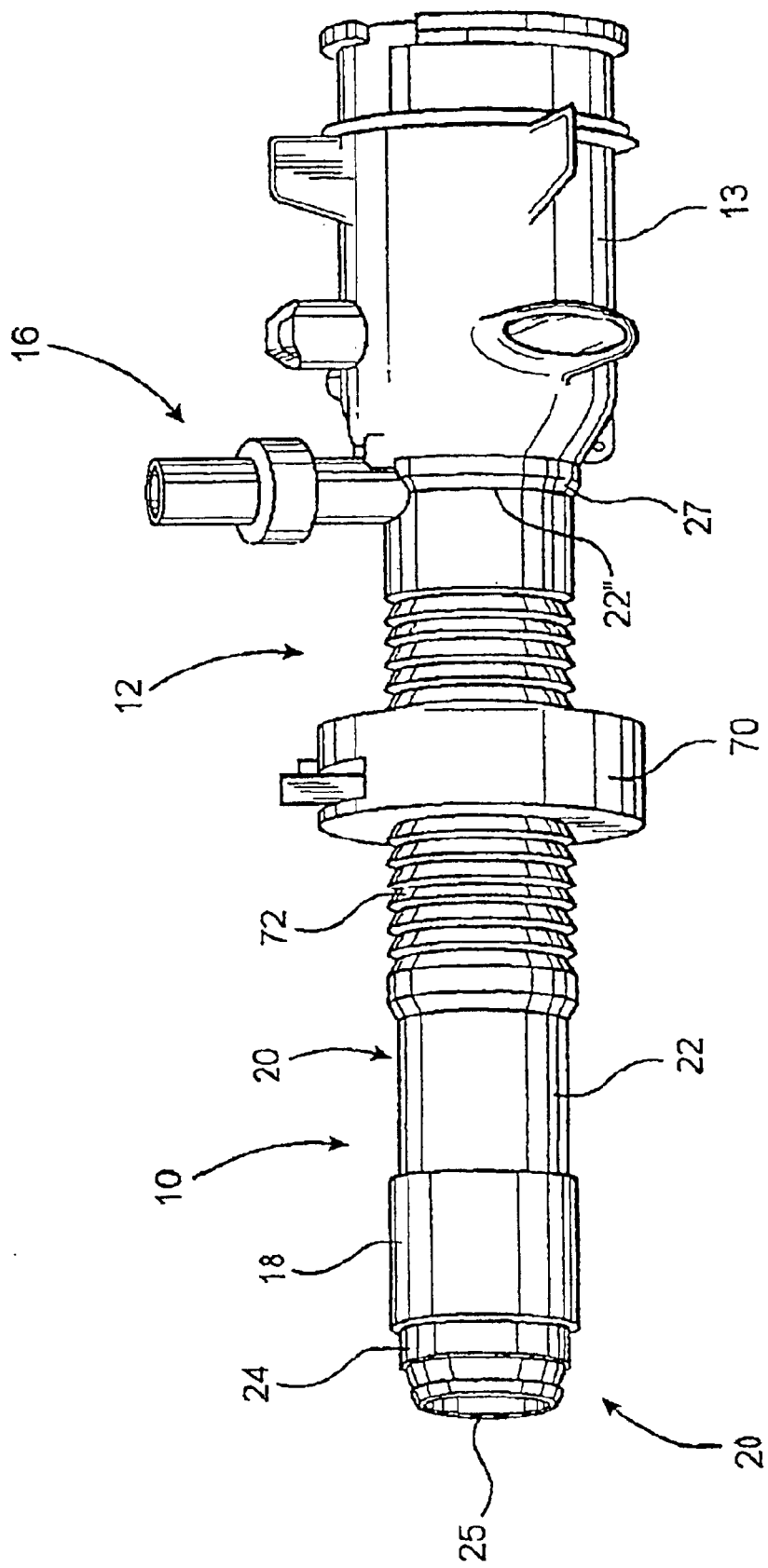
FIG. 1 is a perspective view of a trocar assembly with the anchor assembly of the present invention mounted thereon.

Referring now to FIG. 1, the anchor assembly 10 is of the type which is inflatable by means of directing pressurized fluid thereto through an inlet port generally indicated as 16. As such, the anchor assembly 10 of the present invention includes an inflatable member 18 selectively disposed between a collapsed position, as represented in solid lines in FIGS. 1, 2 and 3, and an inflated, expanded position as represented in phantom lines in FIG. 2. When in its expanded position, the inflatable member 18 extends radially outward from the exterior of the cannula 14. Also, in a most preferred embodiment, the inflatable member 18, whether in its collapsed or expanded position, comprises a substantially annular configuration disposed in surrounding relation to the exterior portion of the trocar 12 and cannula 14 associated therewith. Venting of the inflatable member 18 or removal of the inflating fluid from the interior 19 can be accomplished by manipulation of appropriate valving structure associated with the inlet 16 or other portions of the trocar body 13, as is well known in the art.

One structural feature of the anchor assembly 10 of the present invention is the mechanical securement of the inflatable member 18 to the medical instrument 12 in a manner which is safe, reliable, cost effective and otherwise expeditious from a manufacturing standpoint. The term "mechanical" is meant to be descriptive, in its broadest sense, of securing the inflatable member 18 to the medical instrument 12 in a manner which does not primarily rely on adhesive, heat sealing, exterior binding, or other conventional means of attachment which are currently utilized in the manufacture of medical instruments of this type. However, while the inflatable member 18 is mechanically secured to the exterior cannula 14 or other medical instrument, in a manner to be described in greater detail hereinafter, the use of adhesive or other mounting or attachment devices, compositions or methods may be utilized at least to a minimal extent to maintain certain other components of the anchoring assembly 10 in their intended, operative position.

Accordingly, the various preferred embodiments of the anchor assembly 10 of the present invention include the provision of a mounting assembly, indicated generally as 20 in FIG. 1. In a most preferred embodiment, the mounting assembly 20 includes a first mounting member 22 and a second mounting member 24 disposed on the exterior of the medical instrument, such as the cannula 14, by frictional engagement with the exterior surface thereof or by other appropriate means, which will also be described hereinafter.

The first mounting member 22 is preferably in the form of a sleeve or like structure having an elongated tubular configuration. The length of the first mounting member 22 may vary, but preferably, extends from a location which is inwardly spaced from the distal end or extremity 25 of the cannula 14 to a location generally adjacent or contiguous to the trocar housing 13 or other proximal portion of the trocar or medical instrument 12. In order to facilitate sealing engagement of the first mounting member 22, a sealing device such as, but not limited to, an "O-ring" or like member 27 may be utilized to provide a substantially fluid-tight seal between the proximal end 22' of the first mounting member 22 and the exterior surface of the cannula 14 and/or trocar housing 13, as shown in FIG. 1. In an alternate embodiment of the present invention, the O-ring 27 may be replaced by an adhesive or other sealant material or other appropriate structure for maintaining a fluid tight seal between the proximal 22' and the exterior surface of the cannula 14. The second mounting member 24 is preferably in the form of an annular collar or end cap segment having oppositely disposed open ends. The second mounting member 22 is disposed substantially adjacent and in inwardly spaced relation to the open distal end or extremity 25 of the cannula 14.

Figure 2:
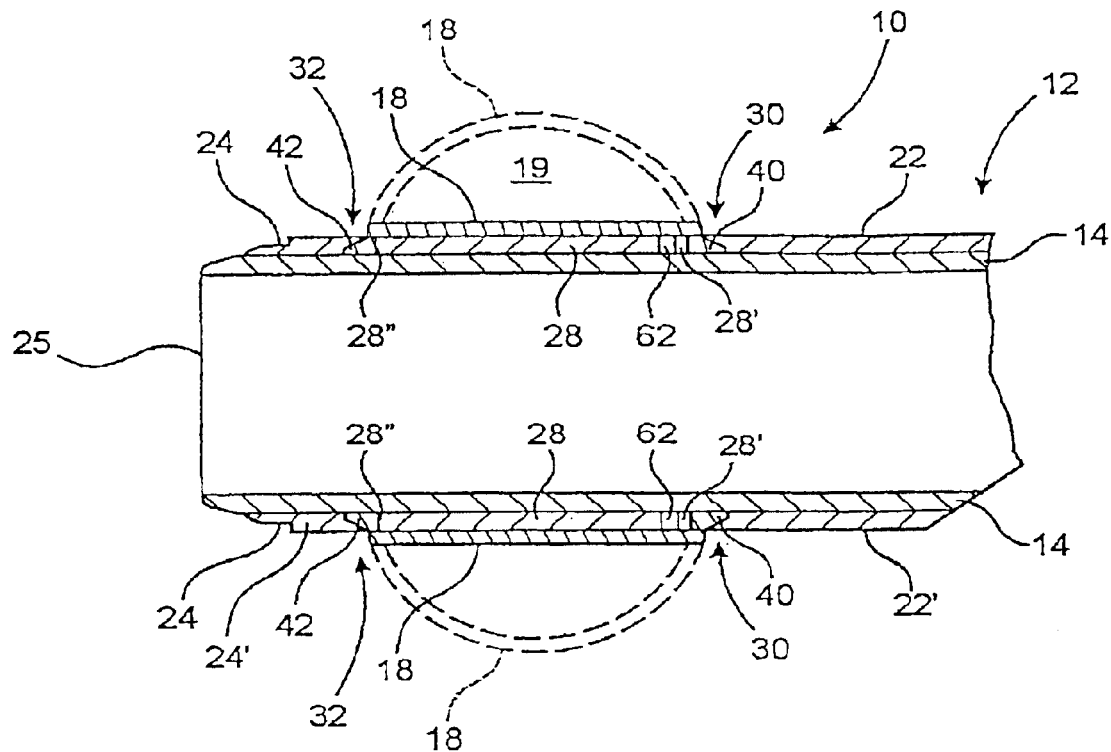
FIG. 2 is a longitudinal sectional view in partial cutaway and phantom showing structural details of at least one preferred embodiment of the anchor assembly of the present invention.
Figure 3:
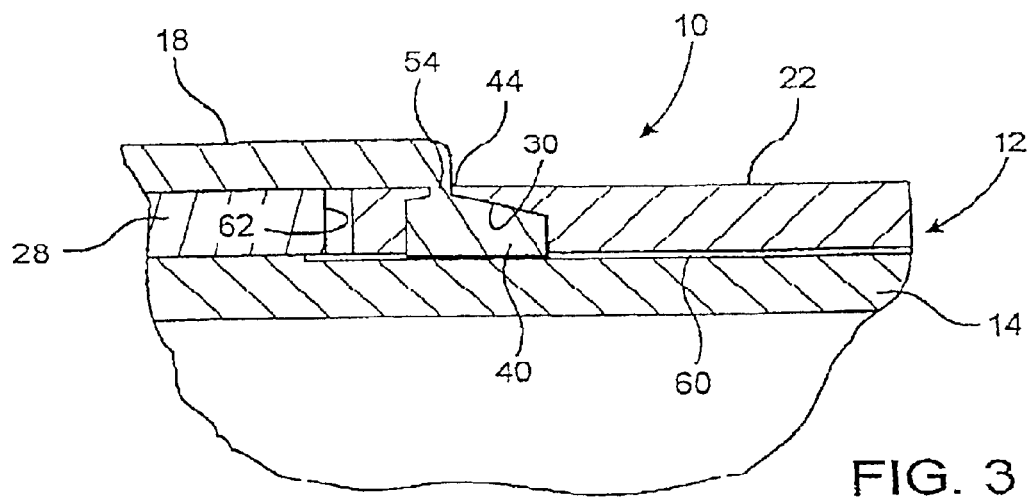
FIG. 3 is a sectional view in partial cutaway showing structural details of a preferred embodiment of the anchor assembly of the present invention including an inflatable member, as disclosed in FIGS. 1 and 2.
Figure 4:
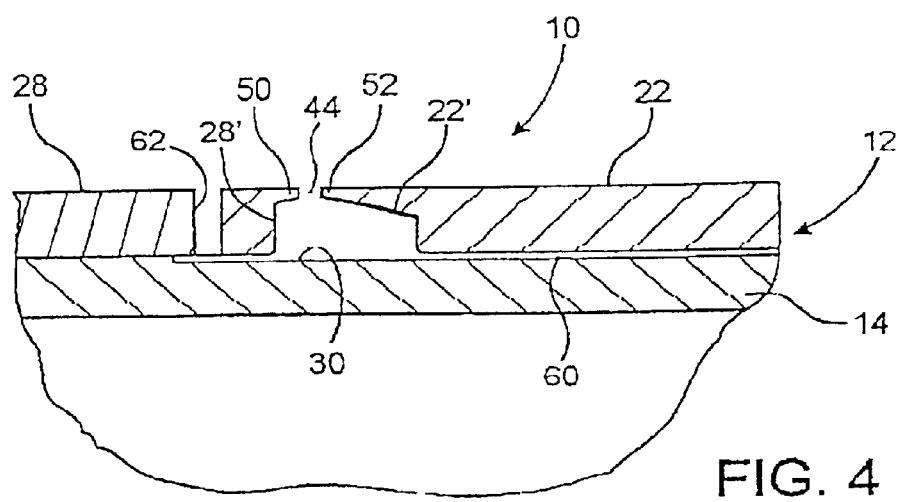
FIG. 4 is a sectional view in partial cutaway of the embodiment of FIG. 3, absent the inflatable member.

Another structural feature of the various preferred embodiments of the present invention is a base 28, which is best illustrated in FIGS. 2–4. The base 28 is directly associated with the secure, mechanical mounting of the inflatable member 18 due at least in part to the predetermined disposition thereof relative to the mounting assembly 20. The base 28 is preferably in the form of an annular bushing disposed in surrounding relation about the exterior surface of the cannula 14. In a most preferred embodiment of the present invention, the annular base 28 includes an inner diameter or dimension that is at least minimally larger than the outer diameter or corresponding dimension of the cannula 14. As such, the base 28 is not fixedly secured to the cannula 14 but rather, is at least minimally spaced from the exterior surface of the cannula 14. This relative dimensioning will facilitate the assembly of the first and second mounting members 22 and 24 and the inflatable member 18 in their intended operative position, as set forth in greater detail hereinafter.

As also disclosed, the base 28 is positioned on the interior the inflatable member 18 and substantially between the inflatable member 18 and the cannula 14. Being so positioned, the interior of the inflatable member 18 is oriented in confronting relation with the exterior surface of the base 28, especially when the inflatable member 18 is in its collapsed position, as best shown in FIG. 2. As is also represented, when the inflatable member 18 is in its outwardly expanded or inflated position it is disposed in outwardly spaced and surrounding relation to the base 28 and the cannula 14.

As disclosed in FIGS. 2 through 4, the first and second mounting members 22 and 24 are mechanically secured to the exterior of the medical instrument 12 or cannula 14 in spaced relation to one another. This relative orientation allows for the positioning of the base 28 between and adjacent to both the first mounting member 22 and the second mounting member 24, albeit in spaced relation thereto, as best shown in FIGS. 3 and 4. This "predetermined spacing" between the base 28 and the mounting members 22 and 24, is more specifically defined by two retaining spaces, generally indicated as 30 and 32.

For purposes of clarity, the structural and operative features of each of the retaining spaces 30 and 32 will be described in detail with particular reference to the one retaining space 30, as disclosed in FIGS. 3 and 4. Accordingly, it is emphasized that the structural and functional details, configurations, dimensions and other pertinent features of the retaining space 30 are substantially the same or generally a structural equivalent of the retaining space 32. Therefore, each of the retaining spaces 30 and 32 are disposed between and at least partially defined by opposite ends of the base 28, as at 28' and 28" and the respective ends of the first mounting member 22, as at 22', and the second mounting member 24, as at 24'. Further, each of the retaining spaces 30 and 32 has an overall, annular configuration extending substantially continuously about the exterior of the cannula 14.

The mechanical mounting of the inflatable member 18 in its intended operative position on the exterior of the medical instrument 12 is further accomplished through the provision of a retaining portion integrally or otherwise fixedly secured to the inflating member 18. More specifically, the retaining portion comprises at least one, but preferably, two retaining segments 40 and 42 each preferably secured to opposite peripheral ends or extremities of the inflatable member 18, as shown in both FIGS. 2 and 3. Each of the retaining segments 40 and 42 are disposed, dimensioned and/or configured to be received within a corresponding one of the retaining spaces 30 and 32. The retaining segments 40 and 42 are thereby securely "gripped" within the retaining spaces 30 and 32, by virtue of being compressed between correspondingly positioned portions of the respective mounting members 22 and 24 and the corresponding ends 28' and 28" of the base 28.

Further, the retaining segments 40 and 42 are formed of a compressible material and may have an overall greater dimension than the corresponding retaining spaces 30 and 32 in which they are respectfully received. Each of the retaining spaces 30 and 32 include an opening 44 disposed in communication with an exterior of the medical instrument 12, as best shown in FIGS. 3 and 4. Therefore, and as set forth above, the corresponding ends 28' and 28" of the base 28 are cooperatively dimensioned, disposed and configured with corresponding portions 22' and 24' of the first and second mounting member so as to not only define the retaining spaces 30 and 32, but also to define each of the openings 44 to have a much lesser dimension than the corresponding retaining spaces 30 and 32. As a result, the retaining segments 40 and 42, being of a larger dimension than the openings 44, cannot pass there through upon the inflatable member 18 being inflated into its expanded position, as represented in phantom in FIG. 2. The retaining segments 40 and 42 are thereby mechanically secured within the retaining spaces 30 and 32 whether the inflatable member 18 is in the collapsed position or the expanded position.

Yet another structural feature of the present invention, as represented in FIGS. 3 and 4 comprises the ends 28' and 28" of the base, as well as the correspondingly positioned portions 22' and 24' of the first and second mounting members 22 and 24, having inwardly directed flanges 50 and 52 respectively. Accordingly, a pair of the flanges 50 and 52 are associated with each of the retaining spaces 30 and 32 and are provided to further restrict the transverse dimension of each of the openings 44. Therefore, while the dimension of the openings 44 are sufficient to allow passage of a connecting segment or link 54 of the inflatable member 18 there through, the dimension of each of the openings 44 are sufficiently reduced to prevent the passage there through of the retaining segments 40 and 42.

In at least one preferred embodiment, the various operative components comprise a substantially circular or annular configuration. More specifically, the various operative components, including the first and second mounting members 22 and 24, the base 28, the inflatable member 18, the retaining spaces 30 and 32, the retaining segments 40 and 42 and the openings 44, all include a substantially continuous configuration as should be evident from the observance of FIGS. 1 and 2.

As set forth above, the positioning of the inflatable member 18 into its expanded position is accomplished by directing a flow of gas or other appropriate fluid, under pressure, into the "interior" 19 of the inflatable member 18. As represented in FIGS. 3 and 4, the inflating fluid is supplied through the inlet 16 and travels along a path of fluid flow which may comprise one or more channels or passageways 60 formed between the cannula 14 and interior surface of the first mounting member 22. In addition, the one or more channels 60 are disposed beneath the retaining segment 40, disposed adjacent to the first mounting member 22, and into one or more outlet ports 62. The outlet port(s) 62 passes through the base 28 and communicates with the interior 19 of the inflatable member 18. As indicated above, at least one embodiment of the present invention may comprise a one or more channels or passages 60 that are disposed in fluid communication with one or more outlets 62 for delivery of the inflating fluid into the interior of the inflatable member 18. In at least one embodiment of the present invention, one or more of the channels or passages 60 are integrally formed so as to be recessed into the exterior surface of the cannula 14. It is emphasized that the length of the passage(s) 60 may vary and extend between the point of communication with the inlet 16 and the point of delivery with outlet 62 into the interior 19. Alternatively, the one or more passages 60 may extend along only a portion of the length of the cannula, such as in the area of and beneath the retaining segment 40.

Figure 5:
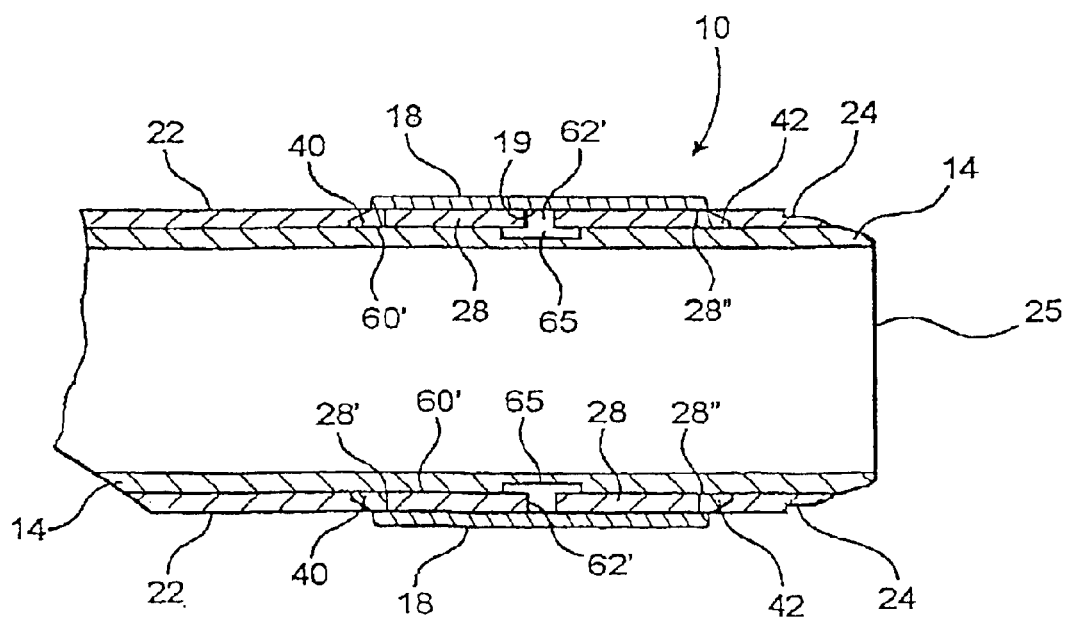
FIG. 5 is a longitudinal sectional view in partial cutaway of yet another preferred embodiment of the anchor assembly of the present invention.
Figure 6:
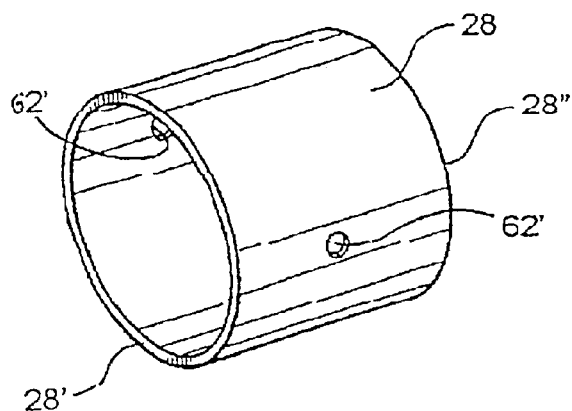
FIG. 6 is a perspective view of a bushing-like base associated with the embodiment of FIG. 5.
Figure 7:
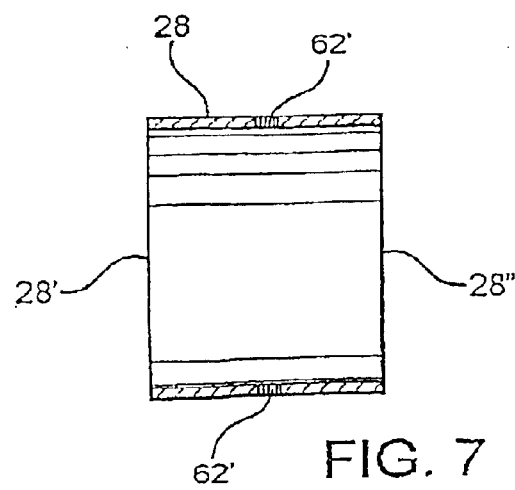
FIG. 7 is a longitudinal sectional view of the embodiment of FIG. 6.

Yet another preferred embodiment of the present invention is disclosed in FIGS. 5 through 7 and relates to a path of fluid flow defined by one or more passages 60' extending beneath and beyond the retaining segment 40 and into communication with a peripheral channel or groove 65. The peripheral groove 65 is formed on the exterior of the cannula 14 and is disposed in direct fluid communication with a plurality of inlets 62'. As disclosed, there are at least two inlets 62' but in is emphasized that the number of inlets 62' may vary. As shown the inlets 62' are formed in a sidewall of the base 28 in a position to direct the inflating fluid from the groove 65 into the interior 19 of the inflatable member 18.

It will of course be noted in FIG. 5 that the depth of the one or more passages 60' is not as pronounced as indicated in the embodiment of FIGS. 3 and 4. In fact, depending on the closeness of the fit between the interior surface of the first mounting member 22 and the exterior surface of the cannula 14, inflating fluid may pass there between without the need for one or more passages 60' to extend along a length of the cannula 14 from the inlet 16 to the peripheral groove 65. However, it is preferred that at least a minimal passage 60' be formed beneath the retaining segment 40 because the engagement of the retaining segment 40 with the exterior surface of the cannula 14 may establish a fluid flow restricting seal. Therefore the existence a path of fluid flow, including the one or more passages 60', is preferably formed in the exterior surface of the cannula 14, so as to allow the inflating fluid to bypass the potentially sealing effect of the retaining segment 40 against the exterior surface of the cannula 14.

As also disclosed, the location of the inlet 62 (see FIGS. 3 and 4) or 62' (see FIGS. 5 through 7) may be located at different positions along the length of the bushing-like base 28. By way of example, in the embodiment of FIGS. 5 through 7 the one or more inlets 62' are substantially centered between opposite ends 28' and 28" of the base 28. To the contrary, in the embodiment of FIGS. 3 and 4 the one or more inlets 62 are located substantially adjacent a proximal end 28' of the base 28.

In the manufacture and production of the anchor assembly 10, the first mounting member 22 is positioned in overlying, surrounding and substantially covering relation to the exterior of the cannula 14. As indicated above, the first mounting member 22 preferably, but not necessarily, extends from the fluid inlet 16, adjacent the body 13 of the instrument 12, to the inflatable member 18, as best shown in FIG. 1. Thereafter, the base 28 with the inflatable member 18 disposed thereon is passed over the distal extremity 25 and forced axially inward towards the first mounting member 22. The retaining segment 40 is thereby compressed and mechanically captured, gripped and secured within the retaining space 30. In such a position, the flanges 50 and 52 associated with the retaining space 30 serve to define the corresponding, opening 44. The connecting segment or link 54, being integrally or fixedly secured between the retaining segment 40 and the remainder of the inflatable member 18 passes through and may be at least partially compressed within the opening 44. Thereafter, the second mounting member or end cap 24 is passed over the distal extremity 25 and a predetermined, constant, axially directed force is exerted thereon, prior to it being fixedly attached, such as by using adhesive. This inwardly directed force serves to compress the end 22" against the O-ring, thereby facilitating its sealing engagement about the cannula 14. This constant axially directed compressive force also serves to compress the retaining segments 40 and 42 within the respective retaining spaces 30 and 32 facilitating the establishment of a secure, mechanical attachment of the inflatable member 18 to the instrument 12.

As set forth above, the mounting of the inflatable member on the cannula 14 or other medical instrument 12 is primarily accomplished by the aforementioned mechanical attachment, comprising the compressed gripping engagement of the retaining segments 40 and 42 within the retaining spaces 30 and 32. However, in order to maintain the preferred mechanical attachment, an adhesive or other means of securement may be used to maintain certain of the operative components in their intended operative position. Therefore in at least one preferred embodiment, the second mounting member or end cap 24, subsequent to having the above noted axially directed force exerted thereon, is secured by an adhesive or other binding material to the exterior of the cannula 14 in its intended position, as shown in FIGS. 1 and 2.

Yet another structural feature of the anchor assembly 10 of the present invention may include the provision of a securement assembly or member, generally indicated as 70. This securement member is fixedly or movably positioned along the exterior surface of the first mounting member 22. While a most preferred embodiment of the present invention has the exterior surface of the mounting member 22 having a somewhat smooth or non-interruptive exterior surface configuration, other configurations may include a stepped or ribbed configuration generally indicated as 72 which facilitates the placement of the securing member or assembly 70. Further, the securement member 70 may be disposed in direct abutting engagement with the exterior surface or skin surrounding the entry site through which the cannula 14 as well at least the portion of the anchor assembly 10 passes. In doing so, the member 70 is preferably formed from a foam or at least semi-flexible or compressible material to resist damage to the exterior surface portions or skin surrounding the entry site.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An anchor assembly structured to retain a medical instrument within a body cavity, said anchor assembly comprising:
    a) a mounting assembly disposed on an exterior of the medical instrument,
    b) a base disposed on the medical instrument in adjacent relation to said mounting assembly,
    c) an inflatable member formed of an elastomeric material and disposable in an expanded position and a collapsed position,
    d) said inflatable member including a retaining portion mechanically secured between said base and said mounting assembly;
    e) said base and said mounting assembly being relatively disposed on the medical instrument to define a predetermined spacing there-between;
    f) said retaining portion of said inflatable member being at least partially disposed within said predetermined spacing between said mounting assembly and said base; and
    g) said retaining portion of said inflatable member being secured in a substantially compressed orientation between said base and said mounting assembly when said inflatable member is in either said collapsed or expanded positions.

2. An anchor assembly as recited in claim 1 wherein said expanded position comprises said inflatable member disposed radially outward from said base and an exterior of the medical instrument.

3. An anchor assembly as recited in claim 1, wherein said retaining portion comprises at least one peripheral segment of said inflatable member, said peripheral segment dimensioned and configured to be retained within said predetermined spacing.

4. An anchor assembly as recited in claim 3 further comprising at least one opening interconnecting said predetermined spacing with an exterior of said mounting assembly and said base.

5. An anchor assembly as recited in claim 4 wherein said at least one peripheral segment comprises a dimension substantially corresponding to said predetermined spacing and sufficiently greater than said opening to restrict passage of said peripheral segment through said opening.

6. An anchor assembly as recited in claim 1, wherein said inflatable member comprises a substantially annular configuration disposed in at least partially surrounding relation to said base; said retaining portion comprising two peripheral segments each disposed at a different opposite end of said inflatable member.

7. An anchor assembly as recited in claim 6 wherein said predetermined spacing comprises two retaining spaces disposed between said base and said mounting assembly, each of said retaining spaces having a different one of said peripheral segments secured therein.

8. An anchor assembly as recited in claim 7 wherein said mounting assembly comprises a first mounting member and a second mounting member each disposed on the medical instrument in spaced relation to said base so as to define said two retaining spaces.

9. An anchor assembly as recited in claim 8 wherein said inflatable member is disposed within said retaining spaces in mechanically gripped engagement between opposite ends of said base and said first and second mounting members.

10. An anchor assembly as recited in claim 1 wherein said mounting assembly comprises, a first mounting member and a second mounting member disposed on an exterior of the medical instrument at a predetermined spacing from said base.

11. An anchor assembly as recited in claim 10 wherein said base is disposed adjacent both said first and second mounting members and into mechanically gripping engagement with said retaining portion of said inflatable member, said retaining portion disposed between said base and each of said first and second mounting members.

12. An anchor assembly as recited in claim 11 wherein said predetermined spacing comprises at least two retaining spaces each disposed between a different one of said mounting members and a correspondingly positioned portion of said base, each of said retaining spaces disposed and configured to secure said retaining portion therein.

13. An anchor assembly as recited in claim 12 wherein said retaining portion of said inflatable member comprises at least two retaining segments, each structured to be compressed within a different one of said retaining spaces so as to be mechanically retained therein.

14. An anchor assembly as recited in claim 13 wherein each of said retaining spaces includes at least one opening, each of said openings disposed in interconnecting relation with a corresponding one of said retaining spaces and an exterior of the medical instrument, said openings disposed and dimensioned to receive a portion of said inflatable member therein.

15. An anchor assembly as recited in claim 14 wherein each of said retaining segments within one of said retaining spaces has a sufficiently greater dimension than a corresponding one of said openings to restrict passage of said retaining segments through said openings.

16. An anchor assembly structured to retain a cannula within a body cavity, said anchor assembly comprising:
   a) a mounting assembly comprising a first mounting member and a second mounting member disposed on the cannula,
   b) a base disposed on the cannula between said first and second mounting members,
   c) two retaining spaces each disposed between a different end of said base and a correspondingly positioned one of said first and second mounting members,
   d) an inflatable member formed of an elastomeric material and disposable between an expanded position and a collapsed position,
   e) said inflatable member including a plurality of retaining segments each mechanically gripped within a different one of said retaining spaces, and
   f) said base being movably disposed on the cannula and axially positionable into compressed engagement with at least one of said retaining segments.

17. An anchor assembly as recited in claim 16, wherein each of said retaining spaces includes at least one opening interconnecting said retaining spaces with an exterior of said mounting assembly and the cannula.

18. An anchor assembly as recited in claim 17 wherein said retaining segments each comprise a dimension substantially corresponding to one of said retaining spaces and being sufficiently greater than a corresponding one of said openings to restrict passage of said retaining segments through said openings.

19. An anchor assembly as recited in claim 16, further comprising a securing member mounted exteriorly of the cannula and disposable in engaging relation with an exterior surface of the body cavity.

20. An anchor assembly as recited in claim 19 wherein said securing member is formed of an at least partially flexible material.

21. An anchor assembly as recited in claim 16, wherein at least a portion of said mounting assembly is, at least initially, movably disposed on the cannula, said mounting assembly and said base axially positionable into compressed engagement with said retaining segments.

22. An anchor as recited in claim 16, further comprising a path of fluid flow extending between and in fluid communication with a fluid inlet and a fluid outlet, said fluid outlet disposed in fluid communication with an interior of said inflatable member and said path of fluid flow disposed and structured to direct inflating fluid from said fluid inlet to said fluid outlet.

23. An anchor assembly as recited in claim 22 wherein said path of fluid flow is disposed between at least a portion of said mounting assembly and said cannula.

24. An anchor assembly as recited in claim 23 wherein said fluid outlet is formed in said base in interconnecting relation between said path of fluid flow and said interior of said inflatable member.

* * * * *